US012690852B2

(12) United States Patent
Farley

(10) Patent No.: US 12,690,852 B2
(45) Date of Patent: Jul. 28, 2026

(54) SURGICAL RETRACTOR WITH INTEGRATED HANDLE AND SYSTEM

(71) Applicant: Thompson Surgical Instruments, Inc., Traverse City, MI (US)

(72) Inventor: Daniel K. Farley, Traverse City, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 300 days.

(21) Appl. No.: 18/481,668

(22) Filed: Oct. 5, 2023

(65) Prior Publication Data

US 2024/0197310 A1 Jun. 20, 2024

Related U.S. Application Data

(60) Provisional application No. 63/432,458, filed on Dec. 14, 2022.

(51) Int. Cl.
| | |
|---|---|
| *A61B 17/02* | (2006.01) |
| *A61B 17/00* | (2006.01) |
| *A61B 17/22* | (2006.01) |

(52) U.S. Cl.
CPC .... *A61B 17/0206* (2013.01); *A61B 17/22031* (2013.01); *A61B 2017/0046* (2013.01); *A61B 2017/22034* (2013.01)

(58) Field of Classification Search
CPC .......... A61B 17/0206; A61B 17/22031; A61B 2017/0046; A61B 2017/22034; A61B 17/02; A61B 2017/0092
See application file for complete search history.

(56) References Cited

U.S. PATENT DOCUMENTS

| | | | |
|---|---|---|---|
| 9,078,635 B2 | 7/2015 | Menendez et al. | |
| 12,171,419 B2* | 12/2024 | McClymont | ........... A61B 17/02 |
| 2008/0183046 A1* | 7/2008 | Boucher | ............ A61B 17/0206 600/232 |
| 2009/0203969 A1* | 8/2009 | Cohen | ................. A61B 17/0206 600/245 |
| 2011/0137130 A1* | 6/2011 | Thalgott | .................. A61B 1/32 600/232 |
| 2012/0296171 A1* | 11/2012 | Lovell | ................ A61B 17/0206 600/213 |

(Continued)

OTHER PUBLICATIONS

"Radiolucent Structural Materials for Medical Applications", Barry Chadwick and Chris Toto, Medical Device and Diagnostic Industry, Jun. 2001, 11 pages.

*Primary Examiner* — Eduardo C Robert
*Assistant Examiner* — Holly Joanna Lane
(74) *Attorney, Agent, or Firm* — McAndrews, Held & Mallloy, Ltd.

(57) ABSTRACT

A retractor system includes a retractor arm and a retractor. The retractor arm includes an elongated member and a retractor connector coupled to an end of the elongated member. The retractor includes a neck, a blade extending from a distal end of the neck, and a nipple protruding from a top side of the neck at a position toward a proximal end of the neck. The retractor connector includes a port configured to receive the nipple of the retractor and couple the retractor to the retractor arm via the nipple. The neck includes a handle between the nipple and the blade.

20 Claims, 9 Drawing Sheets

(56) References Cited

U.S. PATENT DOCUMENTS

| 2014/0364698 | A1* | 12/2014 | Nadershahi | ............ | A61B 1/303 |
| | | | | | 600/215 |
| 2015/0313585 | A1* | 11/2015 | Abidin | ................ | A61B 17/025 |
| | | | | | 600/219 |
| 2021/0145498 | A1* | 5/2021 | Stchur | ................ | A61B 17/1778 |
| 2022/0117592 | A1* | 4/2022 | James | ................ | A61B 17/0206 |

* cited by examiner

SECTION A-A

SECTION B-B

SURGICAL RETRACTOR WITH INTEGRATED HANDLE AND SYSTEM

CROSS-REFERENCE TO RELATED APPLICATIONS

This application claims the benefit of U.S. Provisional Application No. 63/432,458, filed Dec. 14, 2022, the disclosure of which is incorporated herein by reference in its entirety.

BACKGROUND

The present disclosure relates to a surgical apparatus or retractor that retracts soft tissue and other anatomy of a patient in order to provide access to a surgical site.

During a surgical procedure, a practitioner may make an incision in a patient to access internal organs, bones, and/or other anatomical structures. Surgical retractors may be used to hold back soft tissue and other patient anatomy in the immediate area of the incision. Such retractors may provide the practitioner with an unobstructed view of the internal organs, bones, and/or other anatomical structures. Furthermore, the retractors may provide the practitioner with an opening via which the practitioner may access the anatomical structures with one or more surgical tools.

Further limitations and disadvantages of conventional and traditional approaches will become apparent to one of skill in the art, through comparison of such approaches with the present disclosure.

SUMMARY

Various aspects of the present disclosure provide a retractor system comprising one or more surgical retractors that retract anatomy and provide access to a surgical site. For example and without limitation, various aspects of the present disclosure are directed to a retractor system having an retractor arm that may be detachably coupled to a surgical retractor via a retractor connector. In some embodiments, the retractor includes an integrated handle that aids a person in positioning the surgical retractor. Such integrated handle may be especially useful in positioning the surgical retractor prior to attaching the surgical retractor to a retractor connector of a retractor arm.

DETAILED DESCRIPTION

Figure 1:
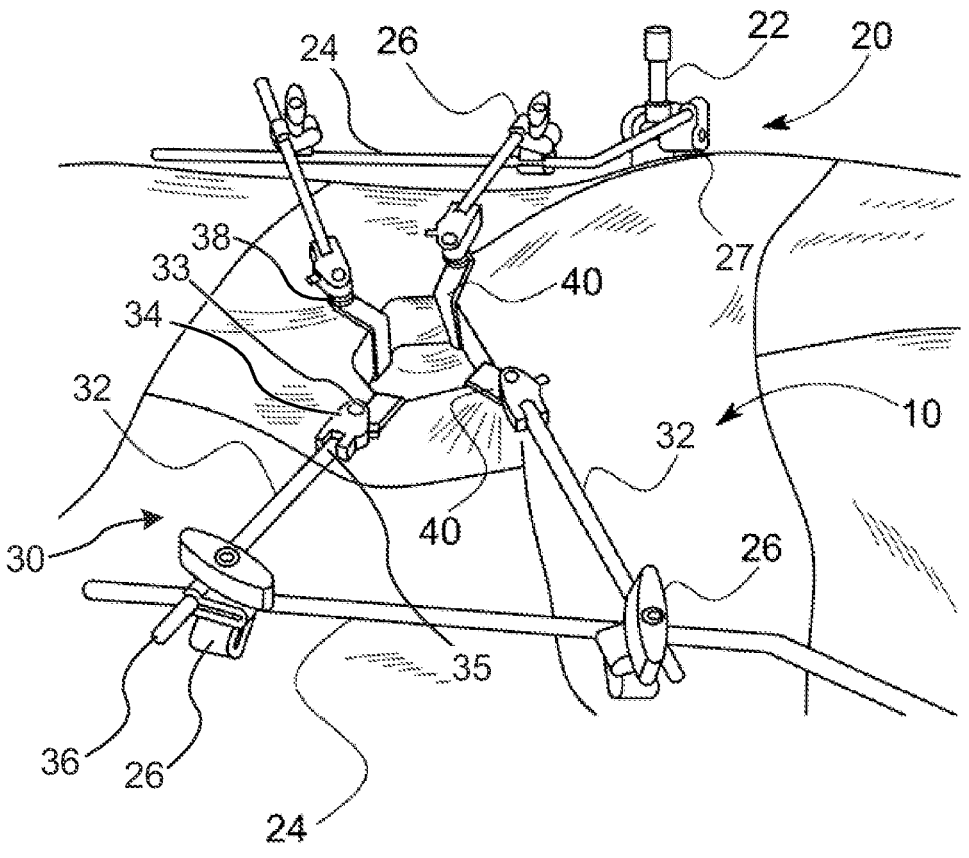
FIG. 1 provides a perspective view of a retractor system in accordance with various aspects of the present disclosure.

Per various aspects of the present disclosure, a retractor system includes a frame to which a proximal end of a retractor arm may be affixed. A distal end of the retractor arm may include a retractor connector that detachably couples to an attachment post or nipple of a surgical retractor and retains the retractor in a desired position. In particular, the retractor may be inserted into a surgical site and positioned via an integrated handle to retract anatomy of the surgical site.

The following presents details regarding various aspects of the present disclosure by way example. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

As utilized herein, "and/or" means any one or more of the items in the list joined by "and/or". As an example, "x and/or y" means any element of the three-element set $\{(x), (y), (x, y)\}$. In other words, "x and/or y" means "one or both of x and y." As another example, "x, y, and/or z" means any element of the seven-element set $\{(x), (y), (z), (x, y), (x, z), (y, z), (x, y, z)\}$. In other words, "x, y and/or z" means "one or more of x, y, and z."

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present disclosure. Similarly, various spatial terms, such as "upper," "lower," "side," and the like, may be used in distinguishing one element from another element in a relative manner. It should be understood, however, that components may be oriented in different manners, for example a semiconductor device may be turned sideways so that its "top" surface is facing horizontally and its "side" surface is facing vertically, without departing from the teachings of the present disclosure.

In the drawings, various dimensions (e.g., lengths, widths, etc.) may be exaggerated for illustrative clarity. Additionally, like reference numbers are utilized to refer to like elements through the discussions of various examples.

Referring now to FIG. 1, an embodiment of a retractor system 10 is illustrated. The retractor system 10 may include a frame assembly 20, one or more retractor arms 30 coupled to the frame assembly 20, and one or more retractors 40 coupled to the retractor arms 30. The various components of the retractor system 10 may be made of stainless steel, radiolucent materials, and/or other materials providing suitable structural and sterilization characteristics.

The frame assembly 20 may include one or more posts 22, one or more frame arms 24, and one or more frame clamps 27. Each post 22 may be fixed to a rail of a hospital bed and/or floor stand such that the post 22 extends upward in a generally vertical direction. Each post 22 may provide a location to which a frame arm 24 may be secured. In the illustrated embodiment, two posts 22 (the second post is out of frame) are secured on opposite sides of a hospital bed, with a frame arm 24 secured to each post 22 by a frame clamp 27. The frame arms 24 may be positioned to generally circumscribe a surgical site. The frame arms 24 may occupy a generally horizontal plane, and may provide a location to which other components of the retractor system 10, such as retractor arms 30 and/or retractor clamps 26, may be affixed.

As further shown, each retractor arm 30 may include an elongated member 32, a retractor connector 34, and a retractor clamp 26. The retractor connector 34 may be attached to a distal end 35 of the elongated member 32 and a retractor 40 may be coupled to the elongated member 32 of the retractor arm 30 via its retractor connector 34. A proximal end 36 of the elongated member 32 may pass through a retractor clamp 26. The retractor clamp 26 may clamp or otherwise affix the elongated member 32 to a frame arm 24 of the retractor system 10. In some embodiments, a retractor connector 34 may be welded, integrated, or otherwise affixed to the distal end 35 of the retractor arm 30. In other embodiments, a retractor connector 34 may be coupled to the distal end 35 of the retractor arm 30 via a pivot or hinge. In such embodiments, the retractor connector 34 may be pivoted or otherwise adjusted with respect to the retractor arm 30 in order to position an attached retractor 40 in a desired position.

As explained in greater detail below, each retractor 40 may include an integrated handle that permits a person to properly position the retractor 40 in a surgical site without the aid of a separately attached handle or retractor arm 30. In various embodiments, the integrated handle may provide sufficient surface area for a person to grasp and impart a substantial retracting force upon the retractor 40 in order to retract anatomical features of the patient and position the retractor 40 in a desired position.

As shown, in FIG. 1, the elongated member 32 of the retractor arm 30 may include a single arm portion (e.g., rod, gear rack, tube, etc.) that permits positioning the retractor connector 34 and attached retractor 40 at a desired distance from a respective frame arm 24. However, the elongated member 32 in some embodiments may comprise a segmented arm having several arm portions (e.g., rods, gear racks, tubes, etc.) that are adjoined to one another via adjustable joints, hinges, and/or angling mechanisms. In such embodiments, the joints, hinges, and/or angling mechanisms may permit adjusting an angle between arm portions of the segmented arm and give the practitioner more freedom in positioning the retractor 40 in a desired position.

FIGS. 2A-2G provide various views of a retractor 200 that is suitable for use as retractor 40 of FIG. 1. The retractor 200 may include a neck 210 and one or more blades 220 that extend from the neck 210. Each blade 220 may comprise a smooth, thin plate that is inserted into an incision to pull back the tissue. The blades 220 may come in many different sizes depending on the particular application and physical characteristics of the patient. The blades 220 may be curved or completely flat, and may have end prongs of various configurations to make it easier to pull back tissue. In some embodiments, the neck 210 and the one or more blades 220 are formed, molded, stamped, or otherwise manufactured as a single, integrated unit.

As depicted, the blade 220 may comprise a distal end 222, a proximal end 224, and a retracting portion 226. The distal end 222 generally corresponds to the end of the blade 220 inserted into an incision of a patient during a surgical procedure, and the proximal end 224 generally corresponds to the end of the blade 220 extending from the incision and out of the patient during a surgical procedure.

The proximal end 224 of the blade 220 adjoins a distal end of the neck 210, thus resulting in the retracting portion 226 generally extending or projecting from the neck 210 toward the distal end 222 of the blade 220. As shown, the retracting portion 226 may form a 90° angle (or a 90° angle±10°) with the neck 410. However, other angles between the retracting portion 226 and the neck 210 are contemplated and may be more suitable for certain surgical procedures. The retracting portion 226 may be sized and adapted to hold back tissue from a surgical site during a procedure. In certain embodiments, the retractor system 10 may include a selection of retractors 200 having differently sized and/or shaped blades 220 to provide increased adaptability for different procedures and/or patients.

The neck 210 may comprise a top side 212, a bottom side 214, and sidewalls 213 between the top side 212 and the bottom side 214. In some embodiments, the top side 212 may be generally planar and the bottom side 214 may be generally planar. Moreover, the top side 212 may be generally parallel to the bottom side 214.

An attachment post or nipple 230 of the retractor 200 may protrude from the top side 212 of the neck 210 from a location toward a proximal end of the neck 210. The nipple 230 may extend upwardly from the top side 212 of the neck 210, whereas the blade 220 may extend downwardly from the top side 212 of the neck 210 at a distal end of the neck 210.

In various embodiments, the neck 210 may be elongated to provide a handle 216 between the distal end of the neck 210 and the nipple 230. Due to such elongation of the neck 210, a person may wrap their hand around the handle 216 and/or grasp the handle 216 with their fingers in order to insert the blade 220 into an incision and properly position the blade 220 within the incision. For certain procedures, a person may need to apply significant force to the handle 216 in order to retract anatomical features of the patient and properly position the blade 220 within the incision. To this end, the top side 212, bottom side 214, and sidewalls 213 of the neck 210 may be formed in a manner conducive to grasping and asserting requisite force via hand and/or fingers. In this regard, the external surfaces of the handle 216 may lack sharp edges. In various embodiments, edges between surfaces (e.g., the edge between top side 212 and sidewalls 213) may be rounded in order to permit grasping and exerting force without injuring a person's hand or fingers.

Furthermore, as alluded to above, the length of the handle 216 between the blade 220 and the nipple 230 may be elongated in order to provide sufficient surface area to grasp and/or a sufficient lever arm to transfer applied force to the blade 220. To this end, the length of the handle 216 may two to six inches long. In some embodiments, the handle 216 is greater than 2 inches, is greater than 3 inches, is greater than 4 inches, is greater than 5 inches, or is greater than 6 inches. Moreover, the neck 210, handle 216, and/or blade 220 may be formed from a radiolucent material to permit greater X-ray visibility of the surgical site despite the elongation of the neck 210.

The nipple 230 may be sized and adapted for attachment to the retractor connector 34 of the retractor arm 30. To this end, the nipple 230 may have a generally cylindrical-shape with a circular cross-section. The nipple 230 may extend from the top side 212 of the neck 210. In one embodiment, a longitudinal axis of the nipple 230 may extend at a right angle from the top side 212. However, the nipple 230 in some embodiments may extend from the top side 212 at other angles.

The nipple 230 may include an upper end 232 and a sidewall 234. The sidewall 234 may include an upper groove 240 and a lower groove 242. The grooves 240, 242 may extend circumferentially around the nipple 230. The diameter of the nipple 230 may be sized such that the nipple 230 may pass through an attachment port 33 of the retractor connector 34.

The upper groove 240 may be positioned along the sidewall 234 of the nipple 430 to vertically align the nipple 230 within the attachment port 33 of the retractor connector 34 in an unlocked position. The lower groove 242 may be positioned along the sidewall 234 of the nipple 430 to vertically align the nipple 230 within the attachment port 33 of the retractor connector 34 in a locked position. A detent or other member of the retractor connector 34 may selectively engage the grooves 240, 242 to respectively position the nipple 230 longitudinally within the attachment port 33 at either the unlocked position or the locked position. Moreover, the grooves 240, 242 may be tapered and/or rounded to aid or guide the retractor connector 34 into engagement with either groove 240, 242, thus helping to longitudinally align the nipple 230 within the attachment port 33 of the retractor connector 34 at either the unlocked position or the locked position.

The retractor 200 may include a serrated surface or teeth 233. Similarly, the retractor connector 34 may include teeth or serrated surface (not shown). In general, the teeth of the retractor connector 34 may engage the teeth 233 of the retractor 200 and prevent rotation of the retractor 200 about the longitudinal axis of the nipple 230 when the lower groove 242 is engaged and the retractor 200 is placed in the locked position. Conversely, the teeth of the retractor connector 34 may disengage the teeth 233 of the retractor 200 and permit rotation of the retractor 200 about the longitudinal axis of the nipple 230 when the upper groove 240 is engaged and the retractor 200 is placed in the unlocked position.

To this end, the teeth 233 of the retractor 200 may be positioned along the top side 212 of the neck 210, along a base of the nipple 230, or at some other location that permits engagement with the teeth of the retractor connector 34 when the retractor 200 is attached to retractor connector 34. Conversely, teeth of the retractor connector 34 may be positioned on a lower surface of the retractor connector 34, along a circumference of the attachment port 33, or at some other location that permits engagement with teeth 233 of the retractor 200 when the retractor 200 is attached to retractor connector 34.

Figures 2A, 2B, 2C, 2D, 2E:
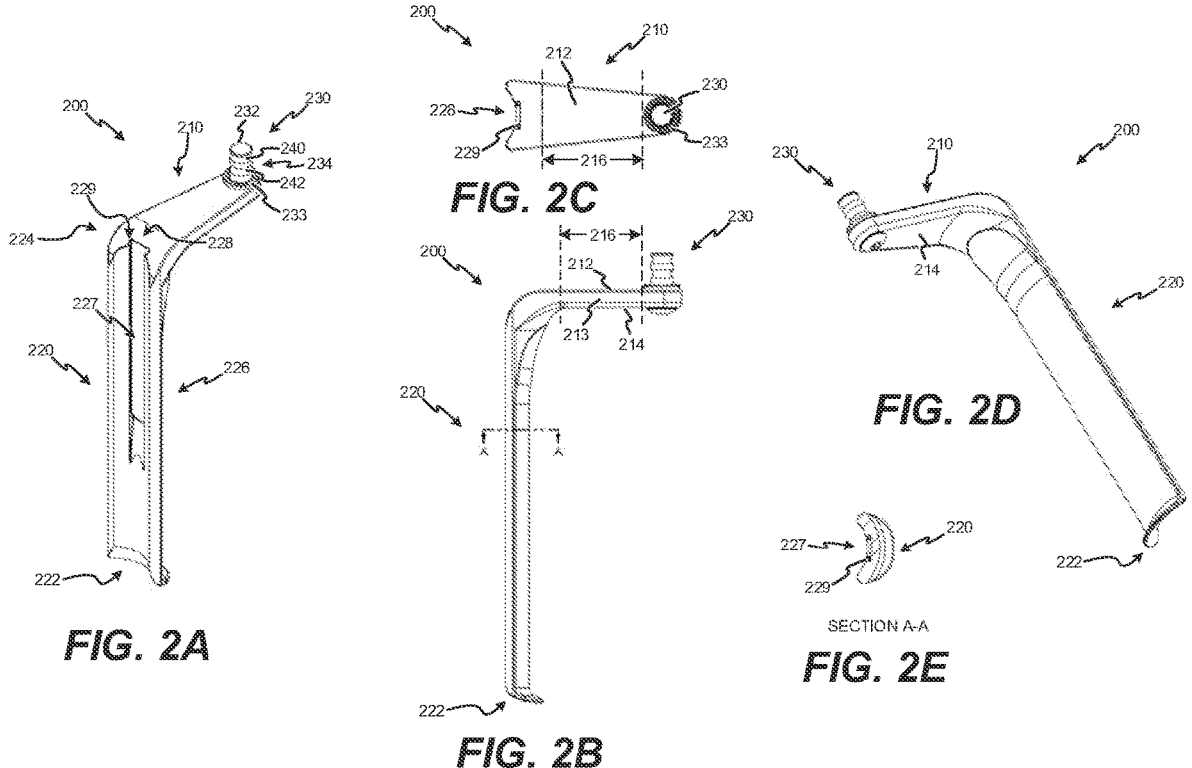
FIGS. 2A-2G provide various views for a retractor of FIG. 1.
Figures 2F, 2G, 3A, 3B, 3C:
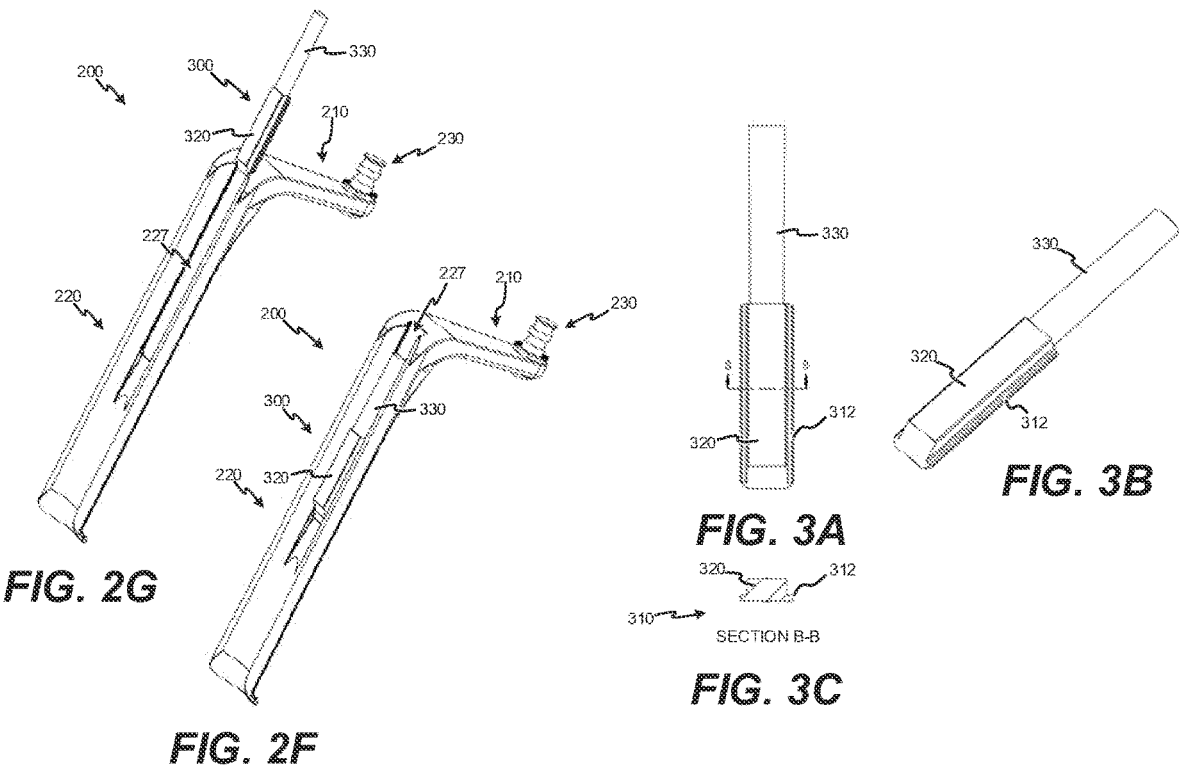
FIGS. 3A-3C provide various views of an accessory that may be received by the accessory channel of the retractor of FIGS. 2A-2G.
Figures 4A, 4B, 4C, 4D:
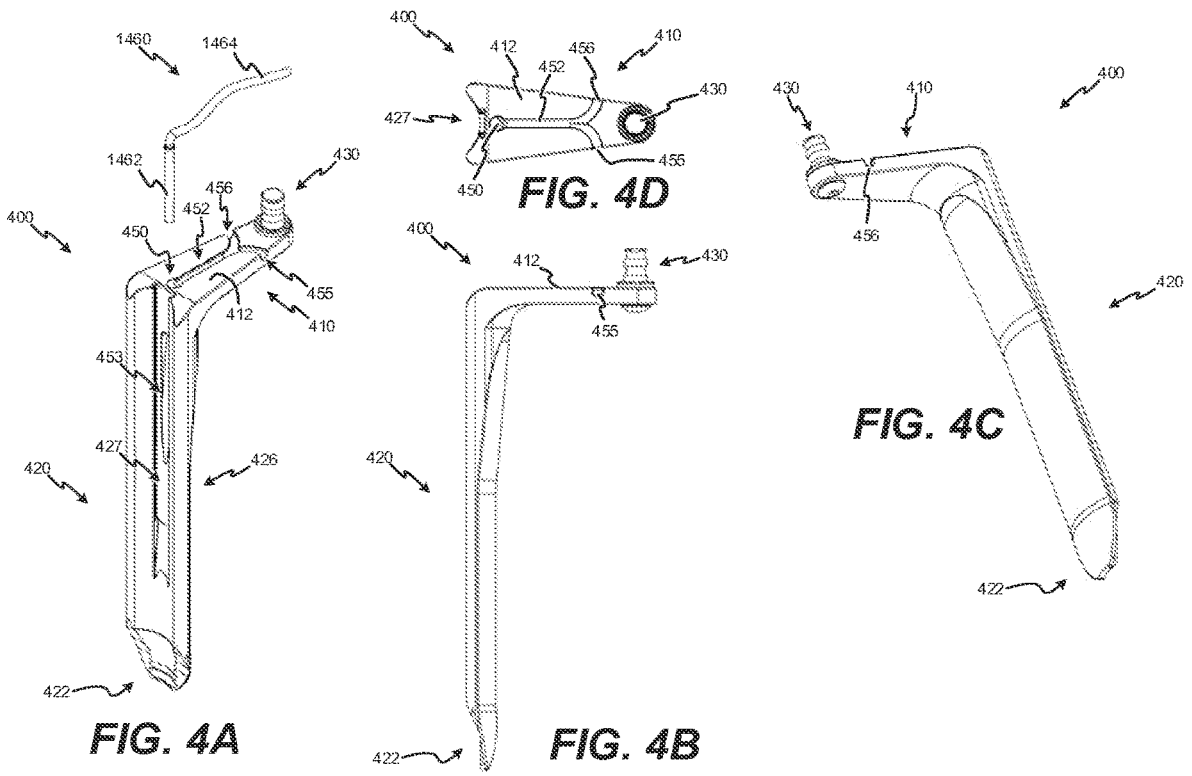
FIGS. 4A-4D provide various views for a retractor of FIG. 1 and an accessory that may be received by an accessory channel.
Figures 5A, 5B, 5C, 5D:
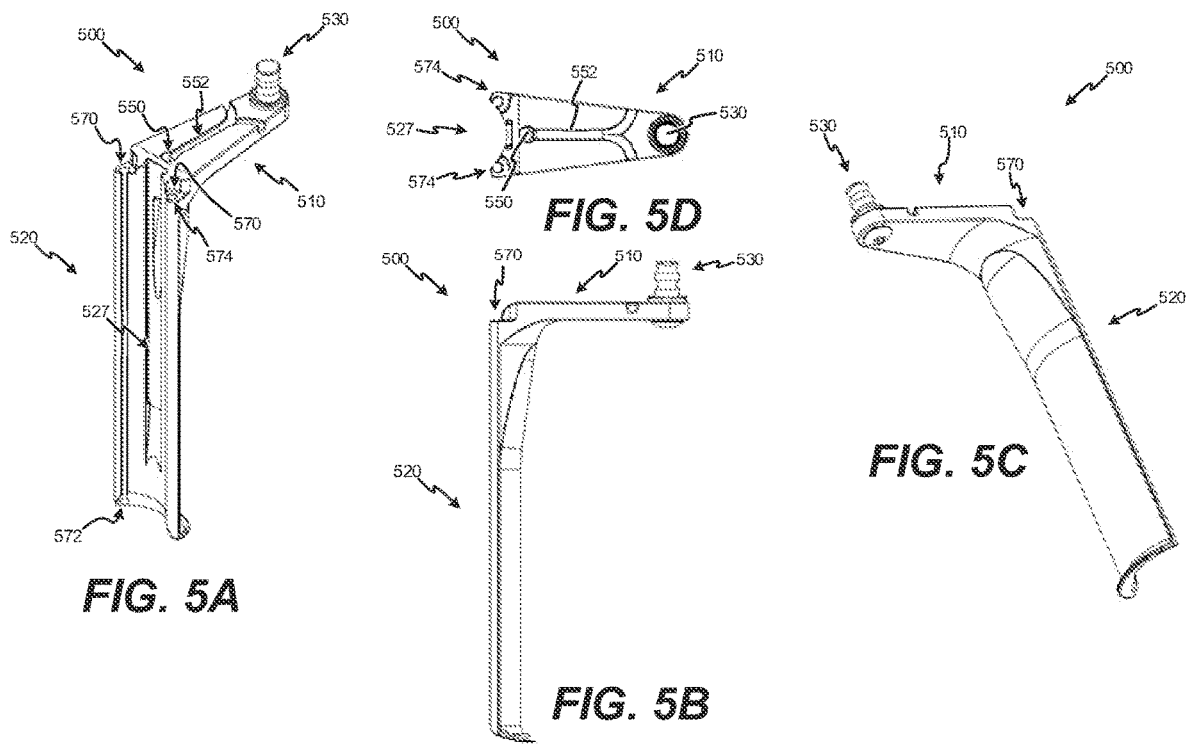
FIGS. 5A-5D provide various views for a retractor of FIG. 1.
Figures 6A, 6B, 6C, 6D:
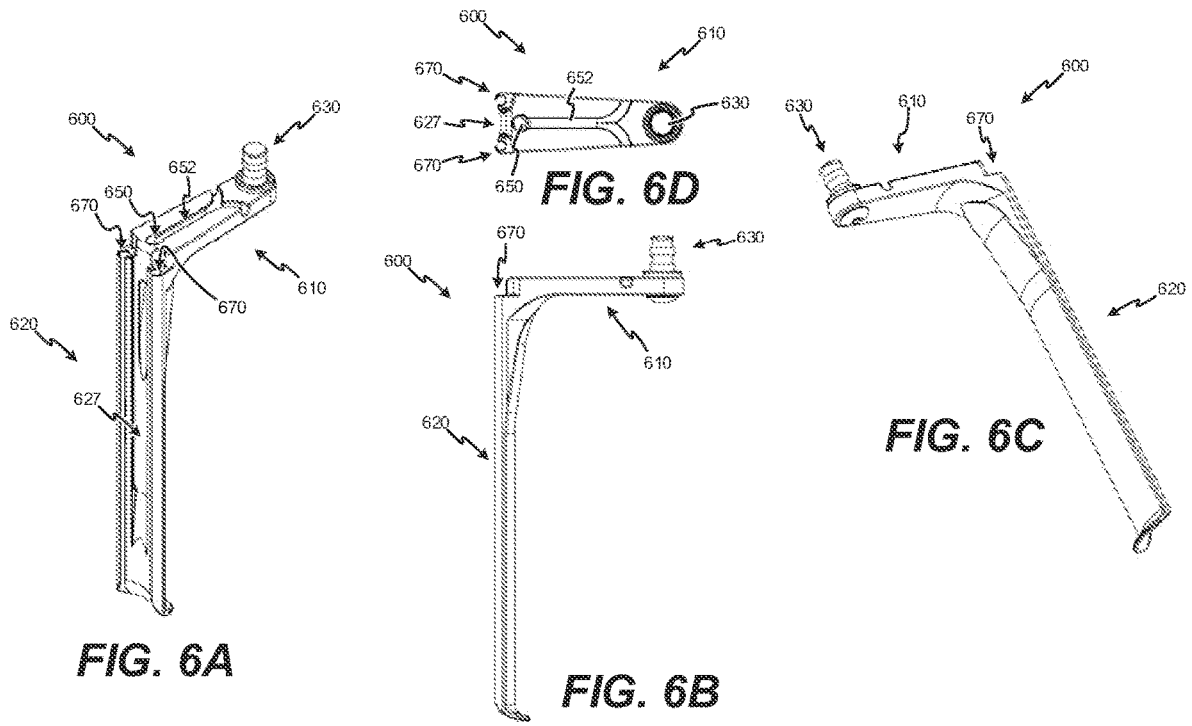
FIGS. 6A-6D provide various views for a retractor of FIG. 1.

As shown, a front side of the retracting portion 226 may include an accessory channel 227 sized to receive an accessory 300 such as a light module shown in FIGS. 3A-3C. However, the accessory channel 227 may be adapted to receive other accessories (e.g., evacuation modules, air modules, etc.) and/or other accessories may be adapted to include features suitable for inserting such accessories into the accessory channel 227. As shown in FIGS. 2A, 20, 2F, and 2G, the accessory channel 227 may include an opening 228 at the proximal end 224 of the blade 220. The opening 228 and accessory channel 227 may be sized to closely mate with a cross-section of the accessory 300. See, e.g., FIG. 3C, which depicts a cross-section 310 of an accessory 300 and FIGS. 2C, 2E, which depict corresponding cross-sections of the opening 228 and accessory channel 227. In some embodiments, the opening 228 may be slightly larger at the proximal end 224 and may taper toward the distal end 222. Such tapering of the opening 228 may ease insertion of the accessory 300 into the accessory channel 227. Moreover, the lower end of the accessory channel 227 may be closed to ensure that the accessory 300 does not inadvertently leave the accessory channel 227 via the distal end 222 of the blade 220.

Referring now to FIGS. 3A-3C, an accessory 300 is shown, that is suitable for insertion into the accessory channel 227 of the retractor 200. The accessory 300 is depicted as a light module. However, other accessories may be implemented with a similar form factor (e.g., a same cross-section 310) so as to permit insertion of such accessories into the accessory channel 227. The accessory 300 may include a body portion 320 and an illumination element 330. The body portion 320 and illumination element 330 may both be sized for insertion into the accessory channel 227 of the blade 220. However, a cross-section 310 of the body portion 320 may be specifically designed to closely match a cross-section of the accessory channel 227. As shown, the cross-section 310 of the body portion 320 may generally comprise a rectangular shape with wings or tabs 312 that extend from lateral sides 314. Such tabs 312 may be received by corresponding grooves 229 in the accessory channel 227. The grooves 229 may retain the body portion 320 within the accessory channel 227 and prevent removal of the body portion 320 from the accessory channel 227 via a direction that is normal to the front side of the blade 220.

Below are described additional retractors 400, 500, 600, 700, 800, 900. Each of these retractors possess aspects similar to the retractor 200. In the interest of brevity, descriptions of such similar aspects will not be repeated. Moreover, reference numerals for retractors 200, 400, 500, 600, 700, 800, 900 have the format 2XX, 4XX, 5XX, 6XX, 7XX, 8XX, 9XX, where the first digit identifies a respective retractor 200, 400, 500, 600, 700, 800, 900 and the XX digits refer to similar features of the retractors. For example, each retractor 200, 400, 500, 600, 700, 800, 900 respectively includes a neck 210, 410, 510, 610, 710, 810, 910. If further description is not provided below for a particular element of retractors 400, 500, 600, 700, 800, 900, then the above corresponding description of the element is presumed to apply to the extent such description aligns with the relevant figures.

Referring now to FIGS. 4A-4D, a retractor 400 is shown, that is suitable for using as the retractor 40 of FIG. 1. Similar to the retractor 200, the retractor 400 may include a neck 410, a blade 420 with a first accessory channel 427, and a nipple 430. As shown, the distal end 422 of the blade 420 may differ from the distal end 222 of the blade 220. In particular, the distal end 222 of the blade 220 may be curved toward a back side of the blade 220, whereas the distal end 422 of the blade 420 may remain straight and inline with the retaining portion 426 of the blade 420.

Moreover, the retractor 400 includes a second accessory channel 450 in addition to the first accessory channel 427. The second accessory channel 450 may conforms to a module portion 1462 of an accessory 1460. In particular, the accessory 1460 may comprises the module portion 1462 coupled to an accessory cable 1464 that each have a circular cross-section. The module portion 1462 may comprise an illumination element, an evacuation elements, an air element, and/or other accessory element to aid a person performing a surgical procedure. Moreover, the accessory cable 1464 may comprise wires, optical fiber, and/or tubes via which control signals, electricity, a vacuum, fluid (e.g., air, medication, etc.), light, etc. may pass to and/or from the module portion 1462. As a result of the accessory channels 427, 450, the retractor 400 may accept accessories 300 having the form factor of FIGS. 3A-3C and/or accessories 1460 having the form factor of FIG. 4A.

The second accessory channel 450 may extend through the neck 410 and into a retaining portion 426 of the blade 420. As further shown, the second accessory channel 450 may extend into the retaining portion 426 and traverse along the first accessory channel 427 in the front side of the blade 420. Moreover, an opening 453 in the front side of the blade 420 may expose a portion of the second accessory channel 450 to the front side of the blade 420. In this manner, the module portion 1462 (e.g., an illumination element) of an accessory 1460 may be placed in the second accessory channel 450 in order to interact (e.g., illuminate) an operative site via the front side of the blade 400.

As further shown, the retractor 400 may include an accessory cable channel 452 that runs along the top side 412 of the neck 410. The accessory cable channel 452 may run from the second accessory channel 450 toward a proximal end of the neck 410. The accessory cable channel 452 may curve near the proximal end of the neck 410 and may exit via a first sidewall opening 455 and/or a second sidewall opening 456. Such exiting via openings 455, 456 may permit the accessory cable channel 452 to guide the cable 1464 along the neck 410 and through either the first sidewall opening 455 or the second sidewall opening 456. In this manner, the accessory cable channel 452 may permit positioning the cable 1464 such that the cable 1464 does not obstruct a surgeon's view.

Referring now to FIGS. 5A-5D, another retractor 500 is shown, that is suitable for using as the retractor 40 of FIG. 1. Similar to the retractor 400, the retractor 500 may include a neck 510, a blade 520 with a first accessory channel 527, a nipple 530, a second accessory channel 550, and an accessory cable channel 552. The retractor 500 may also include two fastener channels 570. In some embodiment, the fastener channels 570 may fully traverse the longitudinal length of the blade 520. In other embodiments, one or more of the fastener channels 570 may only partially traverse the longitudinal length of the blade 520. Further, as shown, the faster channels 570 may be positioned along the lateral sides of the blade 520. However, some embodiments, the blade 520 may include one or more fastener channels 570 positioned at other locations such as along a front side or back side of blade 520. Each fastener channel 570 may include an distal opening 572 toward a distal end of the blade 520 and a proximal opening 574 toward a proximal end of the blade 520. A fastener (e.g., a screw, tapered rod, etc.) may be inserted through each channel 570 via its proximal opening 574. Distal ends of such fasteners (not shown) may extend from the distal openings 572 and be inserted into bone or other anatomical features of the patient in order to further secure the retractor 500 to the patient.

Referring now to FIGS. 6A-6D, another retractor 600 is shown, that is suitable for using as the retractor 40 of FIG. 1. Similar to the retractor 500, the retractor 600 may include a neck 610, a blade 620 with a first accessory channel 627, a nipple 630, a second accessory channel 650, an accessory cable channel 652, and two fastener channels 670. However, a lateral width of the retractor 600 is narrower than a lateral width of the retractor 500. In particular, the neck 610 has a lateral width that is narrower than a lateral width of the neck 510. Further, a lateral width of the blade 620 is narrower than a lateral width of the blade 520.

Figures 7A, 7B, 7C:
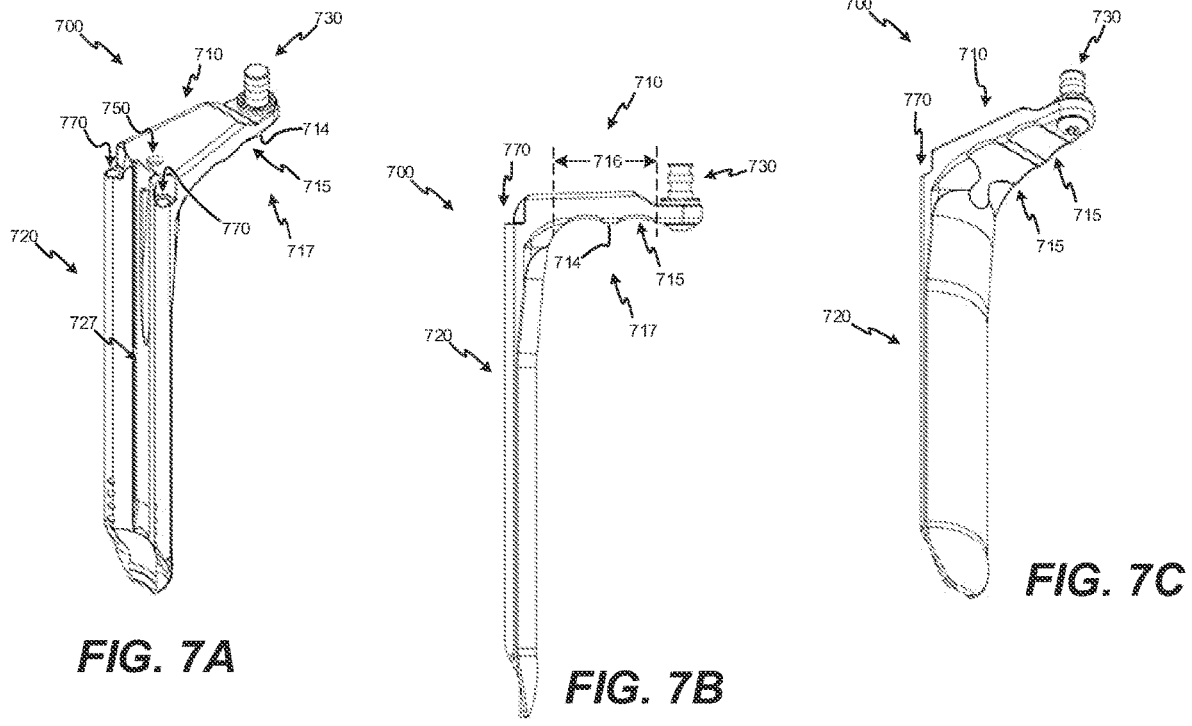
FIGS. 7A-7C provide various views for a retractor of FIG. 1.

Referring now to FIGS. 7A-7C, another retractor 700 is shown, that is suitable for using as the retractor 40 of FIG. 1. Similar to the retractor 500, the retractor 700 may include a neck 710, a blade 720 with a first accessory channel 727, a nipple 730, a second accessory channel 750, and two fastener channels 770. The retractor 700, however, lacks the accessory cable channel 552 of the retractor 500. Moreover, a bottom side 714 of the neck 710 is not planar, but includes one or more depressions 715 that provide a handle grip 717 for the handle 716. In some embodiments, each depressions 715 has a width that generally corresponds to a width of a person's finger. In this manner, the depressions 715 may generally conform to the fingers of a person grasping the handle 716. Such conforming may improve a person's grip upon the retractor 700 and may aid the person in positioning the retractor 700 within an incision.

Figures 8A, 8B, 8C:
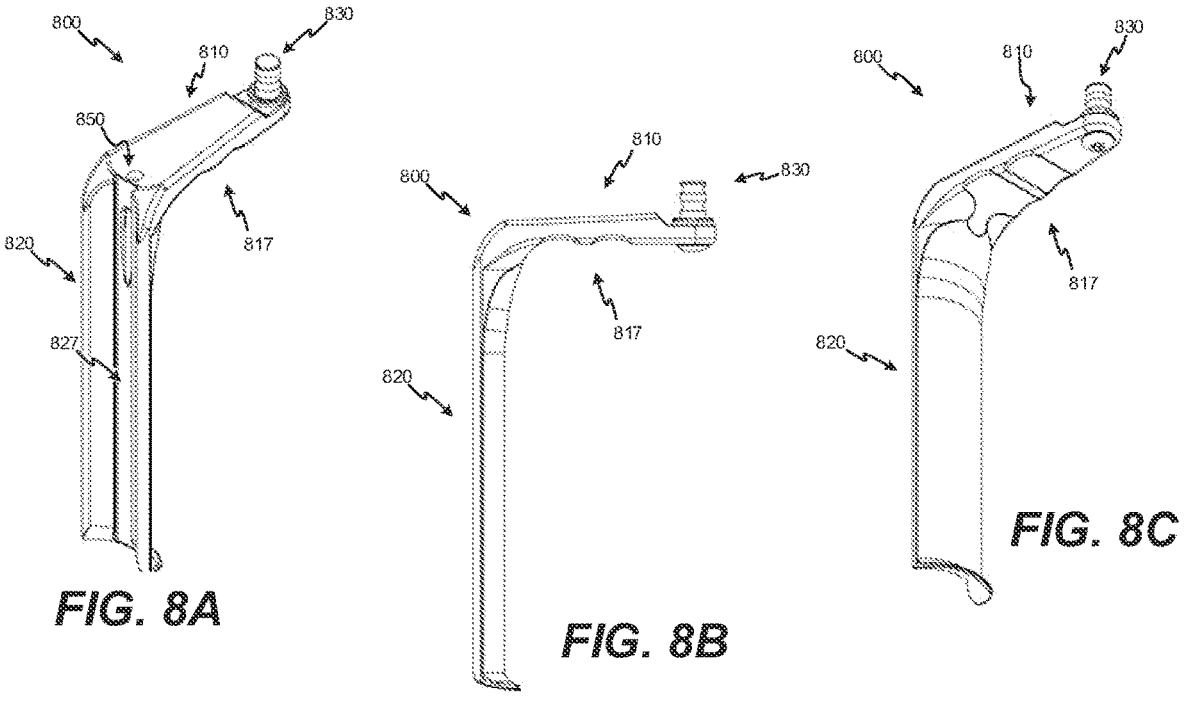
FIGS. 8A-8C provide various views for a retractor of FIG. 1.

Referring now to FIGS. 8A-8C, another retractor 800 is shown, that is suitable for using as the retractor 40 of FIG. 1. Similar to the retractor 700, the retractor 800 may include a neck 810 with a handle grip 817, a blade 820 with a first accessory channel 827, a nipple 830, and a second accessory channel 850. The neck 810, however, is more elongated than the neck 710. As such, the neck 810 provides a hand grip 817 that is longer than the hand grip 717. Such longer length may further aid a person in position the retractor 700.

Figures 9A, 9B, 9C:
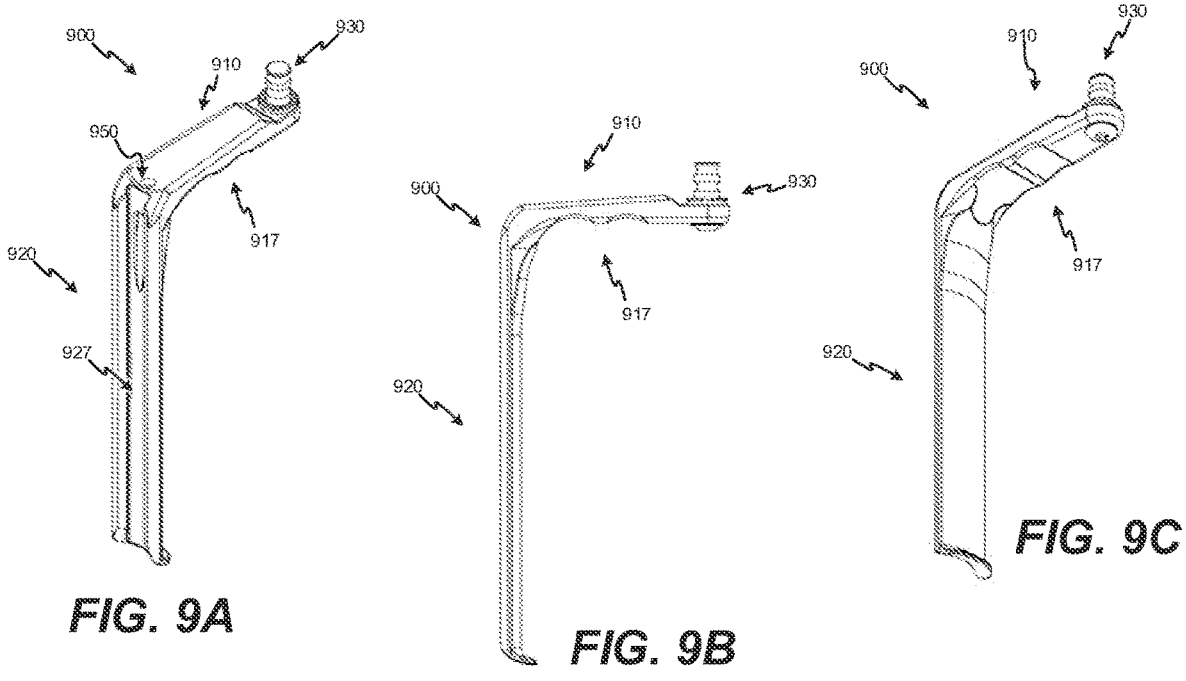
FIGS. 9A-9C provide various views for a retractor of FIG. 1.

Referring now to FIGS. 9A-9C, another retractor 900 is shown, that is suitable for using as the retractor 40 of FIG. 1. Similar to the retractor 800, the retractor 900 may include an elongated neck 910 with a handle grip 917, a blade 920 with a first accessory channel 927, a nipple 930, and a second accessory channel 950. However, a lateral width of the retractor 900 is narrower than a lateral width of the retractor 800. In particular, the neck 910 has a lateral width that is narrower than a lateral width of the neck 810. Further, a lateral width of the blade 920 is narrower than a lateral width of the blade 820.

While particular embodiments of the present disclosure have been shown, it will be understood that the appended claims are not limited thereto since modifications may be made by those skilled in the art, particularly in light of the foregoing teaching. For example, while retractors 200, 400, 500, 600, 700, 800, and 900 have been shown with a specific selection of features, other embodiments may include a different selection of the features from such retractors. It is therefore, the appended claims that define the true spirit and scope of the present disclosure and its embodiments.

What is claimed is:

1. A retractor, comprising:
   a neck comprising a neck top side, a neck bottom side, a neck proximal end, a neck distal end, a neck first lateral sidewall between the neck top side and the neck bottom side, and a neck second lateral sidewall between the neck top side and the neck bottom side, wherein the neck second lateral sidewall is opposite the neck first lateral sidewall, and wherein the neck first and second lateral sidewalls traverse the neck from the neck proximal end to the neck distal end;
   a first sidewall opening in the neck first lateral sidewall and toward the neck proximal end;

an accessory cable channel comprising a channel first sidewall, a channel second sidewall opposite the channel first sidewall, and a channel bottom surface, wherein the channel first and second sidewalls extend into the neck top side to the channel bottom surface, wherein the channel bottom surface laterally spans from the channel first sidewall to the channel second sidewall, and wherein the channel first sidewall, the channel second sidewall, and the channel bottom surface run longitudinally along the neck from the first sidewall opening in the neck and toward the neck distal end;

a blade comprising a blade proximal end couped to the neck distal end and a blade distal end that extends downwardly from the neck distal end;

a nipple on the neck top side and positioned toward the neck proximal end, wherein the nipple protrudes above the neck top side;

wherein the nipple is configured to couple the neck to a retractor connector; and wherein the neck provides a handle between the nipple and the blade.

2. The retractor of claim 1, wherein a length of the handle between the blade and the nipple is greater than 2 inches.

3. The retractor of claim 1, wherein a length of the handle between the blade and the nipple is between 2 inches and 6 inches.

4. The retractor of claim 1, wherein the neck bottom side comprises depressions forming a grip of the handle.

5. The retractor of claim 1, wherein the neck bottom side comprises depressions that conform to a person's fingers.

6. The retractor of claim 1, wherein:

the blade comprises a blade front side that extends longitudinally from the blade proximal end to the blade distal end and an accessory channel in the blade front side; and the accessory channel extends longitudinally between the blade proximal end and the blade distal end and is configured to receive an accessory.

7. The retractor of claim 1, comprising an accessory channel that extends from a hole in the neck top side, through the neck top side, and longitudinally into the blade.

8. The retractor of claim 7, wherein the blade comprises:

a blade front side that extends longitudinally from the blade proximal end to the blade distal end; and an opening in the blade front side that exposes an interior surface of a portion of the accessory channel that extends longitudinally into the blade.

9. The retractor of claim 7, wherein the accessory cable channel extends to the accessory channel.

10. The retractor of claim 9, comprising:

a second sidewall opening in the neck second lateral sidewall and toward the neck proximal end; and wherein the accessory cable channel extends to both the first sidewall opening in the neck first lateral sidewall and the second sidewall opening in the neck second lateral sidewall.

11. The retractor of claim 7, wherein the blade comprises:

a blade first longitudinal side that extends longitudinally between the blade proximal end and the blade distal end;

a blade second longitudinal side that is opposite the blade first longitudinal side and that extends longitudinally between the blade proximal end and the blade distal end; and the blade first longitudinal side comprises a first fastener channel that runs longitudinally between the blade proximal end and the blade distal end.

12. The retractor of claim 11, wherein the blade second longitudinal side comprises a second fastener channel that runs longitudinally between the blade proximal end and the blade distal end.

13. The retractor of claim 11, wherein the first fastener channel comprises a proximal opening configured to receive a fastener and a distal opening configured to permit a distal end of the received fastener to extend from the first fastener channel.

14. The retractor of claim 1, wherein the neck and the blade are radiolucent.

15. The retractor of claim 1, wherein the blade forms a 90° angle±10° with the neck.

16. A retractor system, comprising:

a retractor arm comprising an elongated member and a retractor connector coupled to an end of the elongated member; and a retractor comprising a neck, a blade extending downwardly from a distal end of the neck, a nipple protruding upwardly from a top side of the neck at a position toward a proximal end of the neck, and an accessory channel that extends downwardly through the neck and into the blade;

wherein the retractor connector comprises a port configured to receive the nipple of the retractor and couple the retractor to the retractor arm via the nipple of the retractor;

wherein the neck provides a handle between the nipple and the blade;

wherein the blade encloses a first portion the accessory channel; and wherein an opening in a front side of the blade exposes one or more interior surfaces of a second portion of the accessory channel.

17. The retractor system of claim 16, wherein a length of the handle between the blade and the nipple is greater than 2 inches.

18. The retractor system of claim 16, wherein a bottom side of the neck comprises depressions that conform to a person's fingers.

19. The retractor system of claim 16, wherein:

the retractor comprises an accessory cable channel in the neck; and the accessory cable channel comprises a channel bottom surface that runs from the accessory channel to at least one of a first opening in a first sidewall of the neck and a second opening in a second sidewall of the neck.

20. The retractor system of claim 19, wherein the neck and the blade are radiolucent.

* * * * *